US00PP20757P3

(12) United States Plant Patent
Yam

(10) Patent No.: US PP20,757 P3
(45) Date of Patent: Feb. 16, 2010

(54) ***PHILODENDRON* PLANT NAMED 'LEMON LIME'**

(50) Latin Name: *Philodendron domesticum*
Varietal Denomination: Lemon Lime

(76) Inventor: Tai Yam, 350 Black Springs La., Winter Garden, FL (US) 34787

( * ) Notice: Subject to any disclaimer, the term of this patent is extended or adjusted under 35 U.S.C. 154(b) by 0 days.

(21) Appl. No.: 12/148,328

(22) Filed: Apr. 18, 2008

(65) Prior Publication Data

US 2009/0265825 P1 Oct. 22, 2009

(51) Int. Cl.
*A01H 5/00* (2006.01)

(52) U.S. Cl. ..... Plt./381

(58) Field of Classification Search ..... Plt./381
See application file for complete search history.

*Primary Examiner*—June Hwu

(57) ABSTRACT

A new and distinct *Philodendron* cultivar named 'Lemon Lime' is disclosed, characterized by bright lime-green to golden yellow foliage and unique pink petioles. The new cultivar produces a compact plant form and a busy plant shape, with many leaves and shoots emerging basally.

2 Drawing Sheets

Latin name of the genus and species: *Philodendron domesticum.*

Variety denomination: 'Lemon Lime'.

BACKGROUND OF THE INVENTION

The new cultivar was discovered as a naturally occurring, spontaneous mutation, among several thousand random tissue cultures of *Philodendron domesticum.*

It was discovered by the inventor, Tai Yam, a citizen of Malaysia, in June of 2004, at a commercial laboratory in Nanhai, China. Upon discovery of the interesting mutation, the inventor immediately initiated cultivation in tissue culture in the same laboratory. During the Summer of 2004, 'Lemon Lime' was asexually propagated by tissue culture in a commercial laboratory in Nanhai, China. Subsequently 'Lemon Lime' has been reproduced by micro-propagation and has shown that the unique features of this cultivar are stable and reproduced true to type through several generations.

SUMMARY OF THE INVENTION

The cultivar 'Lemon Lime' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Lemon Lime' These characteristics in combination distinguish 'Lemon Lime' as a new and distinct *Philodendron* cultivar:

1. Bright lime-green to golden yellow foliage
2. Unique light yellow and pink petioles
3. Compact plant form.
4. Bushy plant shape with many leaves and shoots originating from the base of the plant.
5. Prominent yellow to lime green coloration of the stalks.
6. Continuous vigorous growth of shoots from the base, including as the plant ages.

Plants of the new cultivar 'Lemon Lime' are similar to plants of the parent; *Philodendron domesticum* in most horticultural characteristics, however, plants of the new cultivar 'Lemon Lime' have a strong light green/golden color with pink petiole variegation, while the parent has solid foliage in a flat green color. Additionally, the new variety produces more leaves per plant, significantly more growth from the base, a significantly more compact plant and leaves that are more narrow in width and more acute at the apex.

The most similar commercial *Philodendron* hybrid variety available to compare to 'Lemon Lime' is the parent variety, *Philodendron domesticum*. However, one can also make a comparison to the commercial variety *Philodendron* hybrid 'Rojo Congo' (U.S. Plant Pat. No. 14,116). Plants of 'Rojo Conjo' are overall larger and self-heading, rather than vining. 'Rojo Congo' grows much more vigorously, with large, thick leathery foliage, with leaf blades up to 30 cm in length. Foliage of 'Lemon Lime' is much smaller, thinner and of a different color. Additionally 'Lemon Lime' stays much bushier at the bottom of the plant.

BRIEF DESCRIPTION OF THE PHOTOGRAPH

Figure 1:
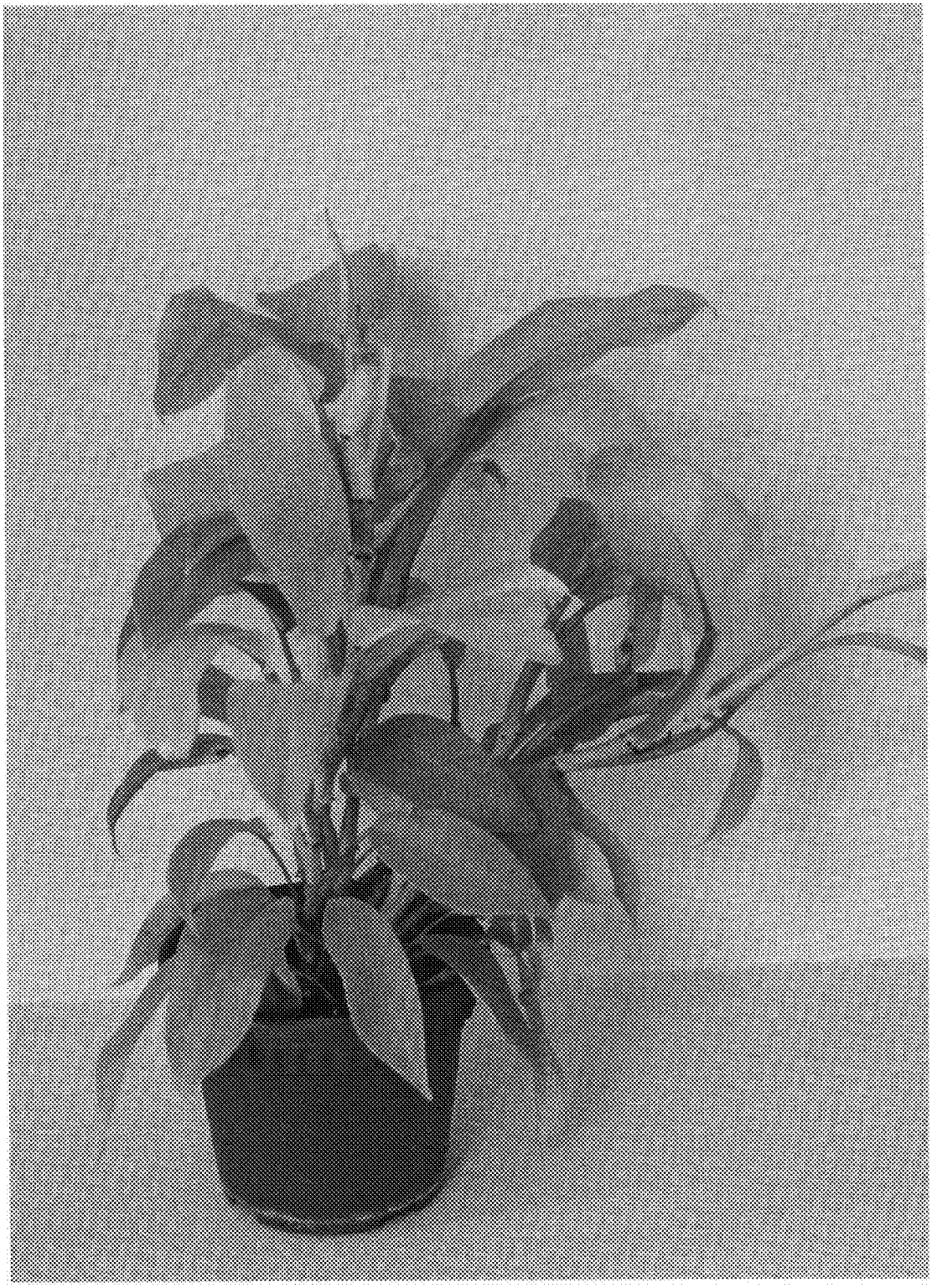

The accompanying photograph in FIG. 1 illustrates in full color a typical plant of 'Lemon Lime' grown in a greenhouse. This plant is approximately 8 months old, shown in a 5 inch pot. The photograph was taken using conventional techniques and although colors may appear different from actual colors due to light reflectance it is as accurate as possible by conventional photographic techniques.

Figure 2:
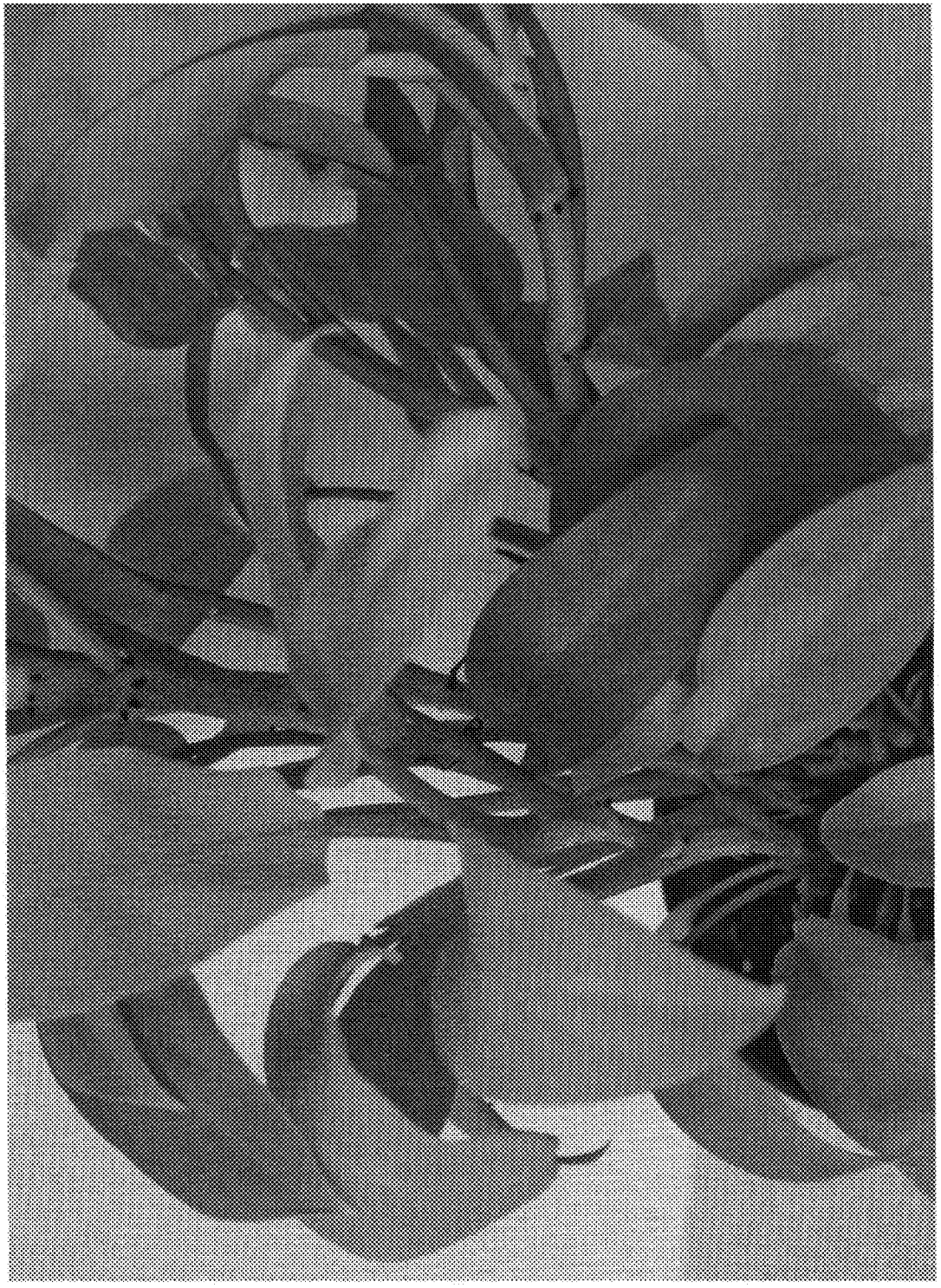

FIG. 2 illustrates in full color typical leaves and petioles of 'Lemon Lime'.

DETAILED BOTANICAL DESCRIPTION

In the following description, color references are made to The Royal Horticultural Society Colour Chart except where general terms of ordinary dictionary significance are used. The following observations and measurements describe 'Lemon Lime' plants grown in a greenhouse in Apopka, Fla., beginning in February of 2007 through January of 2008.

Temperatures ranged from 18° C. to 21° C. at night to 24° C. to 29° C. during the day. Average light measurements ranged from 400 to 800 foot candles during the first 4 weeks, increasing to 1000 to 1500 foot candles during the rest of the growing period. Plants were started in February of 2007 as stage 3 tissue culture plantlets. Measurements and numerical values represent averages of typical plant types.

Botanical classification: *Philodendron domesticum* cultivar 'Lemon Lime.'

PROPAGATION

Time to rooted liner: 3 to 4 months to produce a rooted liner approximately 10 cm tall, with the conditions described above.

Root description: Strong, thick, fleshy roots.

PLANT

Growth habit: Upright tender tropical.

Height: Approximately 30 cm in a 5 inch pot.

Plant spread: Approximately 37 cm.

Growth rate: Slow to moderate.

Branching characteristics: Approximately 50% of branching is basal. With maturity additional branches occur on higher growing points.

Diameter of stem: Approximately .9 cm.

*Stem length.*—Average 20 cm.

*Stem texture.*—Smooth.

*Stem color.*—Near RHS Yellow-Green 145B.

Number of Leaves per stem: Approximately 10.

Age of plant described: Approximately 10 months from a stage 3 tissue culture. Approximately 6 months from a rooted liner.

FOLIAGE

Leaf:

*Arrangement.*—Alternate.

*Average length.*—Approximately 13 cm.

*Average width.*—Approximately 6.2 cm.

*Shape of blade.*—Oblanceolate.

*Apex.*—Acute.

*Base.*—Obtuse.

*Margin.*—Entire.

*Aspect.*—Recurved downward, slightly undulate.

*Texture oftop surface.*—Smooth, slightly leathery.

*Texture of bottom surface.*—Matte, leathery.

*Leaf internode length.*—Occurs in a range between 1 cm to 3 cm.

*Color.*—Young foliage upper side: Near R.H.S. Yellow-Green 150B. Young foliage under side: Near R.H.S. Yellow-Green 145C. Mature foliage upper side: Near R.H.S. Overall coloration appearance is near Yellow-Green 144C. Very fine stripes of Yellow-Green 144A and Yellow-Green N144B.

*Mature foliage under side.*—Near R.H.S. Yellow-Green 145C.

*Venation.*—Type: Pinnate with a highly prominent midrib. Midrib characteristics: Protruding slightly on upperside, significantly on underside. Venation coloration: Mid rib upperside: Near RHS Yellow-Green 144C. Mid rib underside: base and lower ⅓ of length near RHS Red-Purple 59D. Top ⅔ of length near RHS Yellow-Green 146D. Lateral veins upperside: Near RHS Yellow-Green N144B. Lateral veins underside: Near RHS Yellow-Green 1144A.

Petiole:

*Length.*—Average for mature leaf 7.5 cm.

*Width.*—At base .6 cm near leaf blade .4 cm.

*Color upperside.*—Mixed streaks of RHS Yellow 1B and Red-Purple 59C. Yellow coloration is more prominent near the base, Red-Purple is more prominent near the leaf attachment. Underside: Near RHS Yellow 2D with very prominent fine lines near RHS Red-Purple 59B. The Red-Purple coloration is strongest near the leaf attachment.

*Angle.*—Approximately 15° to 30° angle to stem.

*Strength.*—Very strong.

*Texture.*—Very slightly ribbed texture.

*Petiole sheath.*—Shape: Oblanceolate. Length: Average 5.5 cm. Width: Average .4 cm. Color, both sides: Near RHS Yellow 2D with very fine lines near RHS Red-Purple 59B. Texture both sides: Smooth.

Cataphylls: Not consistently present. Occurs on approximately 30% of leaf nodes. More often occurring towards top of plant.

*Shape.*—Oblanceolate.

*Length.*—Average range between 3.5 and 5.5 cm.

*Width.*—Average 1 cm.

*Color.*—Near RHS Yellow 2D with stripes Near Green 143B.

FLOWER

Flowering has not been observed, and is not commercially important in this cultivar.

OTHER CHARACTERISTICS

Disease resistance: Neither resistance nor susceptibility to diseases or pests has been observed in this variety.

Drought tolerance and temperature tolerance: Tender indoor ornamental, not hardy. Tolerates temperatures above 40° C. No tolerance for drought.

Fruit/seed production: Not observed.

What is claimed is:

1. A new and distinct cultivar of *Philodendron* plant named 'Lemon Lime' as herein illustrated and described.

* * * * *